(12) United States Patent
Meredith (10) Patent No.: US 6,424,861 B2
(45) Date of Patent: Jul. 23, 2002

(54) APPARATUS AND METHOD FOR MEASURING THE MOISTURE LEVEL WITHIN ENAMEL DENTINE OR TOOTH TISSUE

(76) Inventor: Neil Meredith, 4 The Bartons, Ashley, Near Box, Wiltshire (GB), SN13 8AL ( * ) Notice: Subject to any disclaimer, the term of this patent is extended or adjusted under 35 U.S.C. 154(b) by 0 days.

(21) Appl. No.: 09/765,438

(22) Filed: Jan. 22, 2001

Related U.S. Application Data (63) Continuation of application No. PCT/GB99/02347, filed on Jul. 20, 1999.

(30) Foreign Application Priority Data

Jul. 20, 1998 (GB) .............................. 9815777

(51) Int. Cl.$^7$ ................................. A61B 5/00
(52) U.S. Cl. ..................................... 600/547
(58) Field of Search ............................... 600/547, 554; 606/41; 433/215

(56) References Cited

U.S. PATENT DOCUMENTS 4,164,214 A    8/1979    Pelzner et al.

FOREIGN PATENT DOCUMENTS

| EP | 0 332 131 | 9/1989 |
|---|---|---|
| EP | 0 446 874 | 9/1991 |

OTHER PUBLICATIONS

Patent Abstracts of Japan vol. 017, No. 105 (P–1495), Mar. 1993 & JP 04 295751 (Kyocera Corp), Oct. 1992.

Patent Abstracts of Japan vol. 1996, No. 07, Jul. 1996 & JP 08 071092 (Lion Corp), Mar. 1996.

Primary Examiner—Max Hindenburg
(74) Attorney, Agent, or Firm—Nixon & Vanderhye P.C.

(57) ABSTRACT

A probe comprising two spaced electrodes is provided between which electrical resistance through enamel, dentine or tooth tissue is measured. The electrodes comprise inner and outer coaxial electrodes spaced by an insulating layer. The diameter of the probe is preferably 1 mm. The tip of the probe may be shaped to match the surface being measured. The signal from the probe is A to D converted for analysis. The rate of change of resistance gives a measure of the rate of change of moisture level (porosity). The porosity is related to tooth sensitivity and so the system can provide an objective measurement of tooth sensitivity.

25 Claims, 6 Drawing Sheets

Insulator
Electrode 1
Electrode 2

APPARATUS AND METHOD FOR MEASURING THE MOISTURE LEVEL WITHIN ENAMEL DENTINE OR TOOTH TISSUE

This application is a continuation of PCT/GB99/02347, filed Jul. 20, 1999.

BACKGROUND OF THE INVENTION

1. Field of the Invention

This invention relates to an apparatus and method for measuring the surface and subsurface level of moisture within and permeability and/or porosity of enamel, dentine or tooth tissues by measuring the resistance or conductivity of the enamel, dentine or tooth tissue and its rate of change with time. The method and apparatus according to the invention can also be used to determine tooth sensitivity.

2. Discussion of Prior Art

The moisture levels of tooth tissue vary depending on external and internal parameters. Externally the moisture level depends on the level of fluid in the environment (humidity) and the type of tooth tissue being tested, enamel being a dry highly crystalline material and dentine being a collagenous material with a higher moisture level.

A measurement of moisture level in enamel, dentine or tooth tissues is of value in determining the efficacy of adhesive bonding agents for tooth filling materials.

Dentine also has a large number of tubules passing from the inner pulp to the junction between enamel and dentine. Fluid can pass along these tubules and tooth pain and sensitivity are attributed to this flow which may be induced by application of heat, cold and solutions which change the osmotic potential. A number of dental treatments related to the reduction of tooth sensitivity aim to block the dentinal tubules and reduce the fluid flow. A measurement of the level and rate of change of surface moisture level relates to the flow of fluid through dentine tissue and tubules and is therefore of use in providing a means of predicting the sensitivity of teeth or the efficacy of treatment designed to reduce sensitivity.

The moisture level can also be used to give an indication of how close the pulp tissue is to the dentine being measured. This information is valuable in determining how to treat the tooth.

SUMMARY OF THE INVENTION

Devices are known that measure the electrical resistance of teeth in the diagnosis of caries. Enamel is generally a good insulator, however, during the carious process, cavities form in the tissue which fill with saliva, the ions of which set up conductive pathways causing resistance values to fall. Thus, a measure of the conductivity of the tooth is an indication of the presence of caries. Such devices typically comprise an electrode which is coupled to a surface of the tooth that has been dried, and a second electrode which the patient holds in their hand. A summary of some of these known devices can be found in the paper "Re-evaluation of Electrical Resistance Measurements for the Diagnosis of Occlusal Caries" by Ricketts et al. published in the British Dental Journal of Jan. 7, 1995.

Although such devices can be used for predicting the presence or absence of caries, the wide separation of the electrodes mean that it is difficult if not impossible to accurately predict the conductive path taken by the current. Thus, the device is not suitable for measuring the moisture level of specific areas of the tooth tissue. Furthermore, although it can be used for monitoring the large change in resistance associated with the presence or absence of tooth caries, it is not accurate or fast enough to detect smaller changes in conductivity.

U.S. Pat. No. 4,164,214 discloses an apparatus for measuring the sensitivity of teeth. This apparatus involves inserting a ground lead into the patient's mouth and contacting the patient's teeth with an oral probe. The electrical output of the oral probe is increased until the patient feels a tingling or warm sensation whereupon the patient acts to stop the increase, the value of the electrical output at this point is an indication of tooth sensitivity. This device relies upon the patient to record the moment they can feel the sensation. The level of feeling at which the patient stops the increase may vary from patient to patient and even from day to day with one patient. Thus, there is a disadvantageous level of subjectivity in the results obtained. The device relies upon nervous stimulation to operate which is a major disadvantage.

In accordance with one aspect of the present invention there is provided an apparatus for measuring the moisture level within enamel, dentine or tooth tissues, comprising: a probe having two electrodes arranged such that in use they both contact the enamel, dentine or tooth tissue under test; an electrical power source connected between the two electrodes; a sensor for sensing the voltage or current produced by said power source across or through the test sample; and a signal processor responsive to said measured voltage and/or current to calculate a value indicative of said moisture level within said enamel, dentine or tooth tissues, wherein the two electrodes are arranged coaxially with an insulator layer separating them and the diameter of the tip of said probe is less than 5 mm.

Thus, the present invention alleviates the disadvantages of the prior art by providing an apparatus comprising a probe having two electrodes that can be placed a known distance apart on the tooth tissue to accurately measure the conductivity or resistance and from this determine the moisture level of the tooth tissue located between the two electrodes. A measurement of the rate of change of conductivity with time provides an indication of the rate of change of moisture level and provides an objective indication of tooth sensitivity.

The two electrodes are arranged coaxially with an insulator layer separating them. This arrangement of the electrodes gives a compact easy to use probe which in use encloses a specific desired area of dental tissue between the two electrodes allowing the moisture level of this area of the tissue to be measured.

A small diameter of the probe at the contact surface, means that the moisture level in a small precise area can be measured. Furthermore, in such a probe the distance between the electrodes is small, thereby enabling areas of low moisture level and high resistance to be accurately measured.

In one embodiment the contact surface of the electrodes is flat, whereas in another the probe tip is convex. A good contact between the tooth tissue and electrode is important, thus it is advantageous for the contact surface of the electrodes to have a shape that is complementary to that of the tooth tissue to be measured.

In a further embodiment the tip of the probe is conical. Such a shape allows the insertion of the probe into the tooth tissue and thus this probe can be used for subsurface measurements.

In one embodiment the power source is an AC source, preferably a sinusoidal current source (although a square wave source could be used). An AC source reduces possible problems of distortion due to polarisation of the test sample. A current source means that only the resultant voltage need be measured.

In preferred embodiments the apparatus is bandwidth limited and the signals are filtered to reject extraneous interference. Thus, the apparatus may be made less sensitive to interference from other sources.

Advantageously the apparatus comprises a full wave rectifier, low pass filter and an analogue to digital converter to convert the analogue signal to a digital signal. The value of the digital signal provides a direct indication of moisture level.

In one embodiment the analogue to digital converter is a 16 bit or greater analogue to digital converter, preferably with a sampling rate of at least 100 Hz. A high resolution analogue to digital converter means that the apparatus is suitable for use across a wide range of resistances, typically from 100 Ohms to 100M Ohms and hence a wide range of moisture levels. A high sampling rate means that rapid changes in moisture levels can be accurately recorded.

Advantageously, the input impedance of the analyser is greater than 1 GOhms. A high input impedance of the analyser enables it to accurately measure moisture level even where the resistance of the tooth is quite high.

Preferably the apparatus comprises data storage means for storing calibration data. Thus, the apparatus can be calibrated for different probes and for different situations. It can for example be calibrated so that the resistance/conductivity measurements made by the apparatus are translated directly to moisture level. Alternatively the device can be calibrated so that the rate of change of these measurement can be translated to tooth sensitivity by measurement of rate of change of moisture level.

In one embodiment the signal processor of the apparatus is adapted to calculate tooth sensitivity from the variation in the measured values over time. The apparatus can thus be directly used to produce an objective measure of tooth sensitivity.

Preferably the apparatus comprises display means for displaying the calculated moisture level and/or tooth sensitivity, advantageously said display means is graphical and is adapted to display the moisture level as it varies with time.

In preferred embodiments the apparatus comprises an alarm that is set to be activated when the measured values exceed or fall below at least one preset value.

According to another aspect of the present invention there is provided, a method of measuring the moisture level of enamel, dentine or tooth tissues comprising the steps of: removing excess surface saliva from an area to be tested of the enamel, dentine or tooth tissues; contacting said test area with a probe having two electrodes; connecting an electrical power source between the electrodes; measuring the current or voltage produced by said electrical power source through or across said test area; calculating a value indicative of the moisture level of said test area from said measured values, wherein the two electrodes are arranged coaxially with an insulator layer separating them and the diameter of the tip of said probe is less than 5 mm.

In preferred embodiments the electrical power source is an AC power source and the method further comprises the step of converting the AC signals to DC signals. The use of an AC power source prevents the sample from becoming polarised, however a DC signal is easier to interpret, thus the method provides for the conversion of the signal.

BRIEF DESCRIPTION OF THE DRAWINGS

Embodiments of the present invention will now be described, by way of example only, and with reference to the accompanying drawings, in which.

DETAILED DISCUSSION OF EMBODIMENTS

Figure 1:
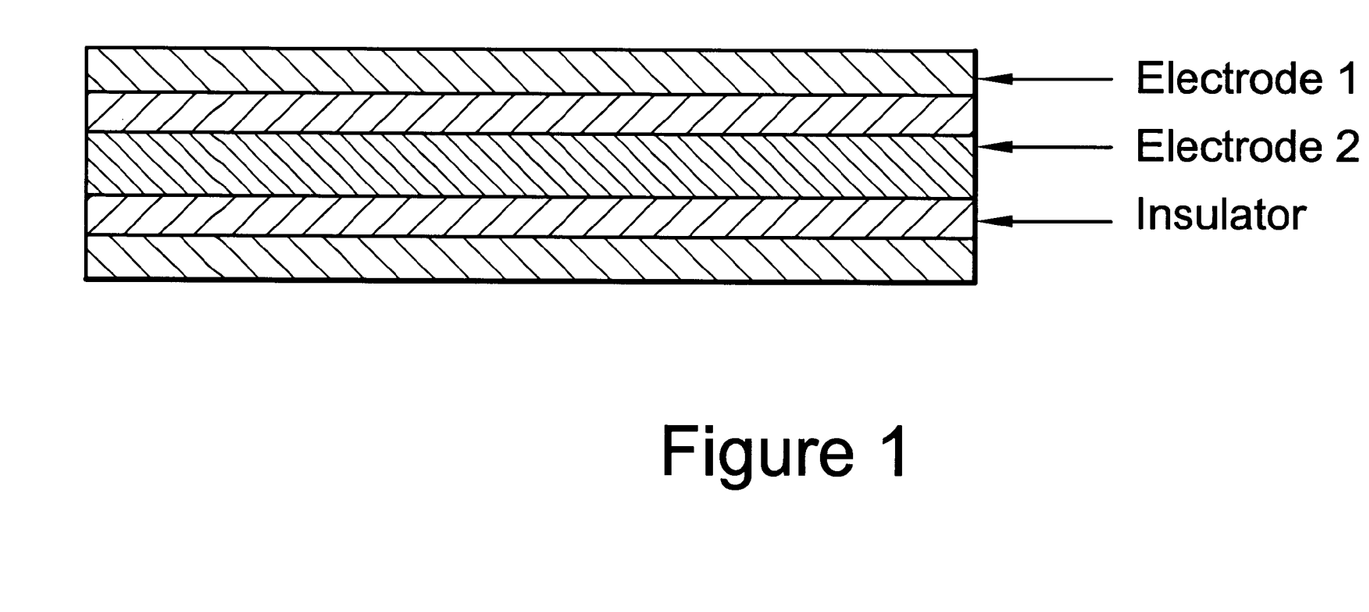
FIG. 1 illustrates a probe according to one embodiment of the invention.

With reference to FIG. 1, a coaxial probe with a flat contact surface, suitable for measuring the moisture level on a flat surface of dental tissue is shown. The probe tip has a diameter of <1 mm, the width of the outer electrode is 0.1 mm, and the diameter of the inner electrode is 0.4 mm. The inner electrode is formed from a piece of silver wire, the outer electrode being formed from a hollow length of the stainless steel tube. The insulating layers are formed from epoxy resin.

Figure 2A:
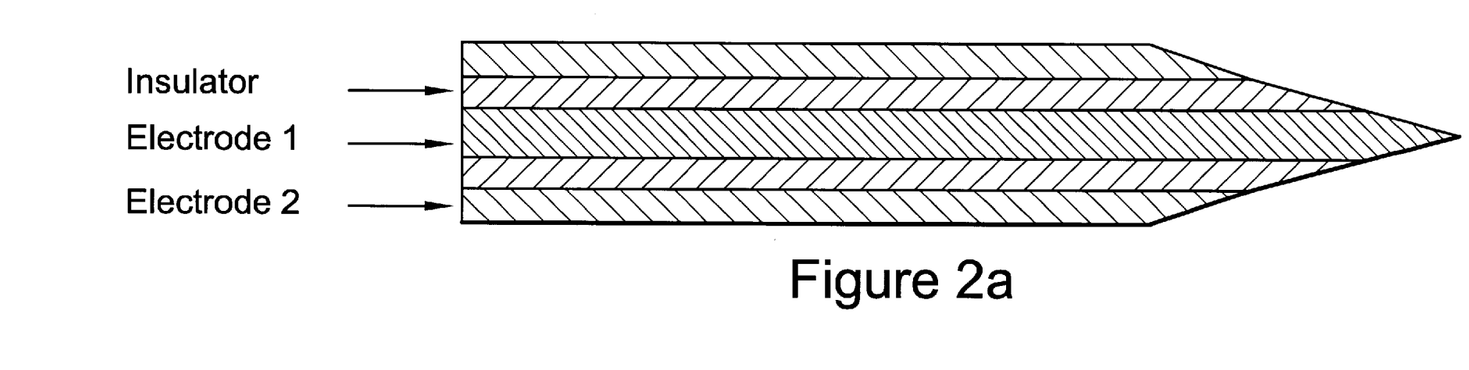
FIGS. 2a and 2b are longitudinal and transverse cross-sections of another embodiment of the invention.
Figure 2B:
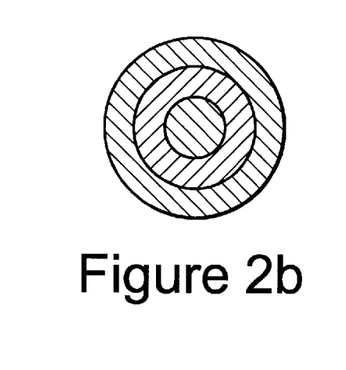

FIGS. 2a and 2b show longitudinal and transverse cross-sections of an alternative embodiment of the probe, comprising a conical tip. This probe is specially adapted for subsurface moisture measurements. The dimensions and manufacture of this probe is similar to the probe shown in FIG. 1.

Alternative embodiments of the probe, not illustrated, can have different shaped tips depending on the shape of the dental tissue under investigation. The shape of the probe tip is designed to complement the shape of the area of dental tissue under investigation, thereby providing a good contact between probe and dental tissue. For example, a probe having a convex tip is used to measure the moisture level of dental tissue with a concave surface.

Figure 3:
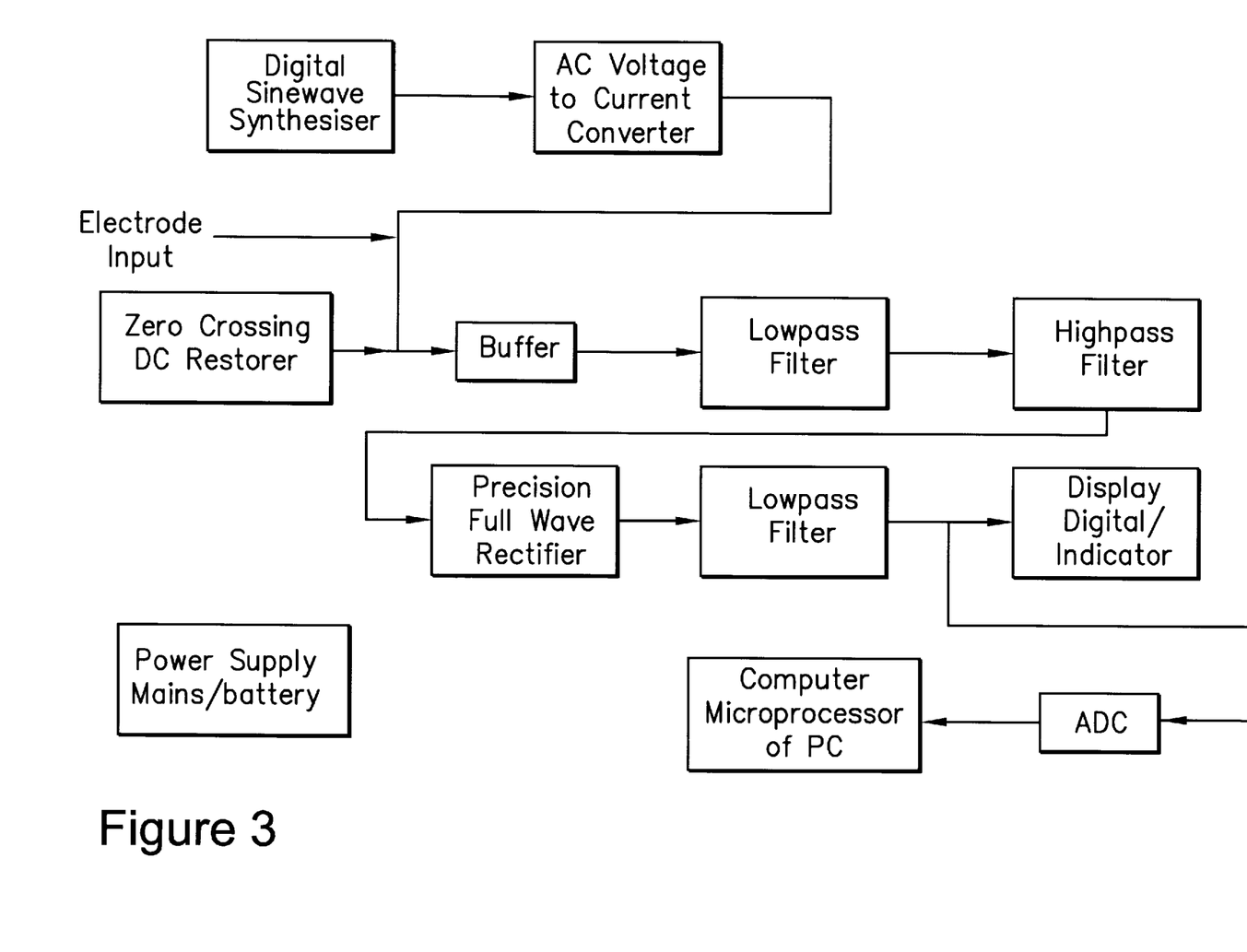
FIG. 3 illustrates a block diagram of the electronic circuitry of an embodiment of the invention.

With reference to FIG. 3, a device according to an embodiment of the invention comprising an electronic instrument designed to measure the AC electrical resistance and its rate of change across a small area of dental tissue is illustrated in a block diagram. The instrument relates these measured values directly to moisture level, or to tooth sensitivity, i.e. indirectly to rate of change of moisture level.

Figure 4:
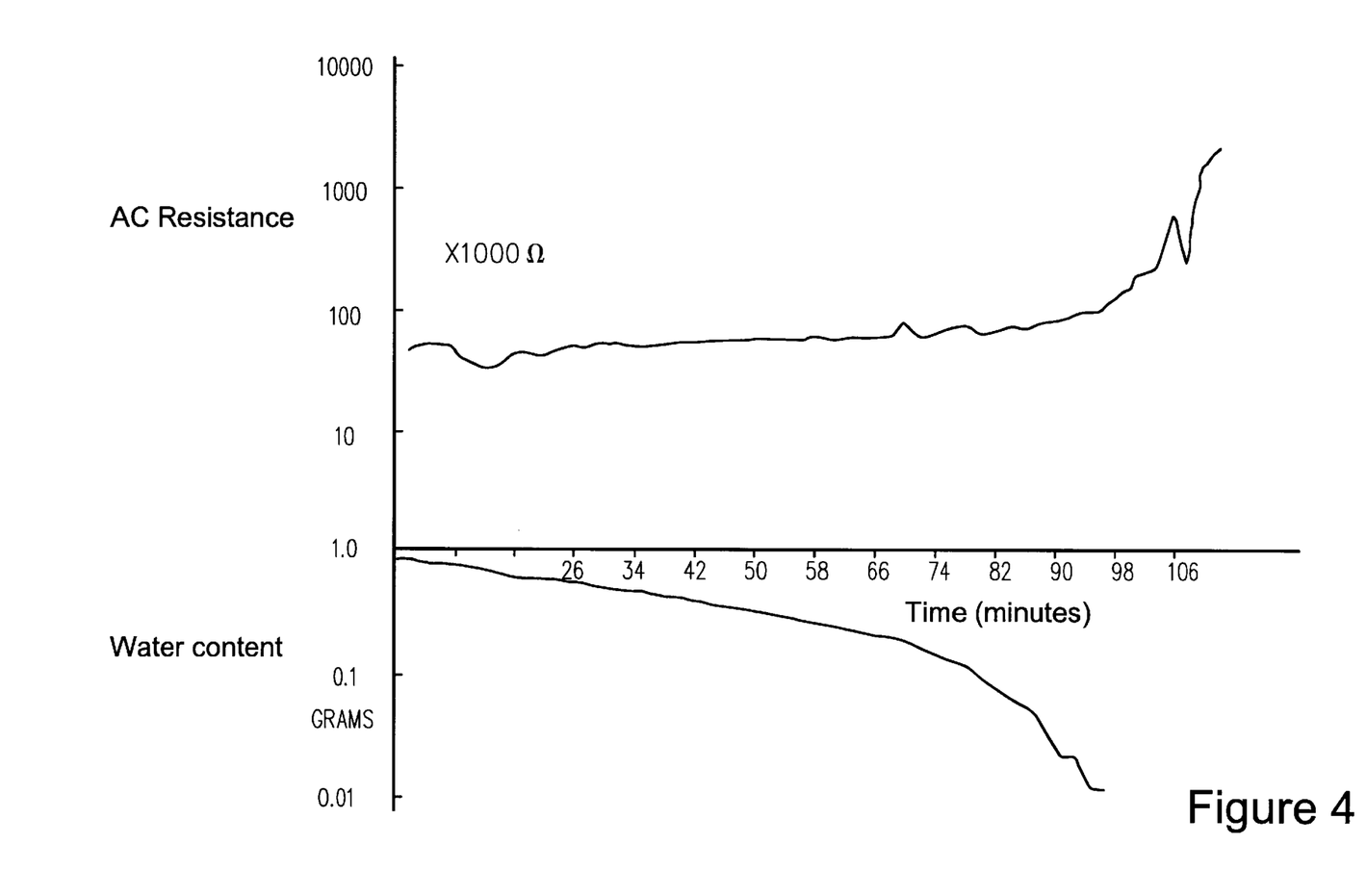
FIG. 4 illustrates the rate of change with time of AC resistance and mass of a water saturated piece of filter paper left to dry.

The analyser determines the resistance of the tooth tissue by applying a low current, typically <0.5 $\mu$A, sinusoidal drive to the test sample via a coaxial electrode. The resistance is given by the ratio of the voltage across the test sample divided by the drive current. This value is directly related to moisture level and can be converted to it by, for example, calibration. The graph of FIG. 4 illustrates the correlation of moisture level and resistance by showing the variation in mass of a water saturated piece of filter paper as it dries and the corresponding changes in its resistance with time.

The test range of the instrument is wide ranging from 100 Ohms to 100M Ohms and the input impedance of the analyser is greater than 1 GOhms. The input test leads of the probe are of low capacitance. The system bandwidth is limited and the signals are filtered to reject extraneous interference. A precision full wave rectifier and filter converts the AC voltage into a DC signal representing the value of the resistance and hence also indicative of the value of the moisture level. The test results may be inverted to give a measure of conductance.

The DC signal may be displayed on a digital or bargraph display or LED (i.e. red/green) and high or low limit trips may be set to sound or indicate alarms at preset intervals.

The DC signal is then quantised by an analogue-to-digital converter thereby providing a means for logging data and plotting changes in moisture level with time. The instrument also includes a timing circuit to measure the time taken for a predetermined moisture level to be reached. The device further comprises a microprocessor for performing the signal processing and other processing functions, such as calculating moisture level or tooth sensitivity from the measured values of voltage and/or current and their rate of change with time. The device comprises a graphical display for displaying the results calculated by the processor. The unit is powered by a mains power source. Alternative embodiments may be powered by disposable or rechargeable batteries.

The device further comprises data storage means for storing calibration data, which is located in a memory within the microprocessor. This data is typically obtained from clinical measurement related to known measurement of resistance or conductance and absolute levels of moisture measured related to specimen weight. Further data relating rate of change of moisture level to tooth sensitivity is also stored.

Figure 5:
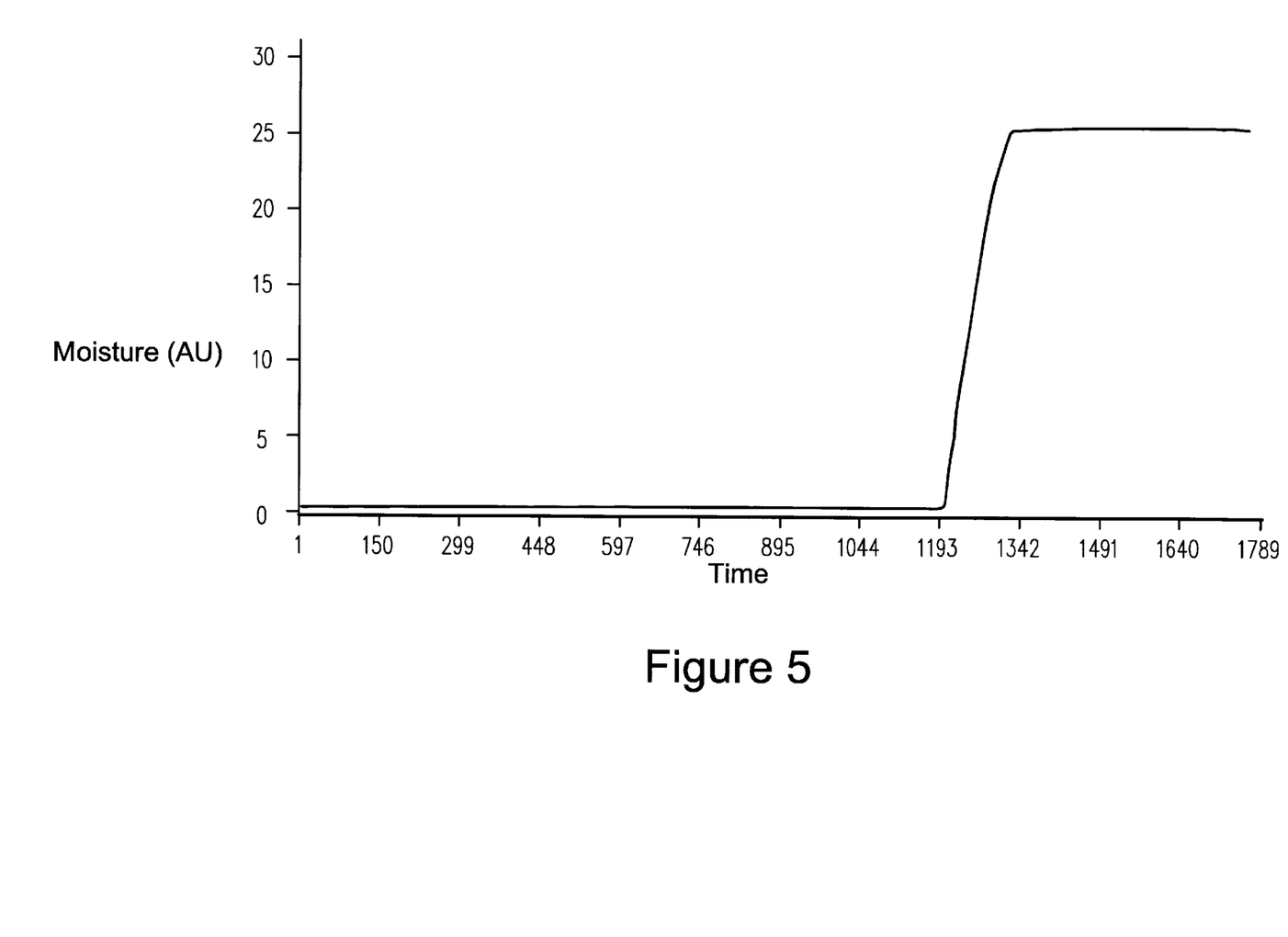
FIG. 5 illustrates the rate of change with time of the moisture level of dental tissue with no smear layer measured using an apparatus according to an embodiment of the invention.
Figure 6:
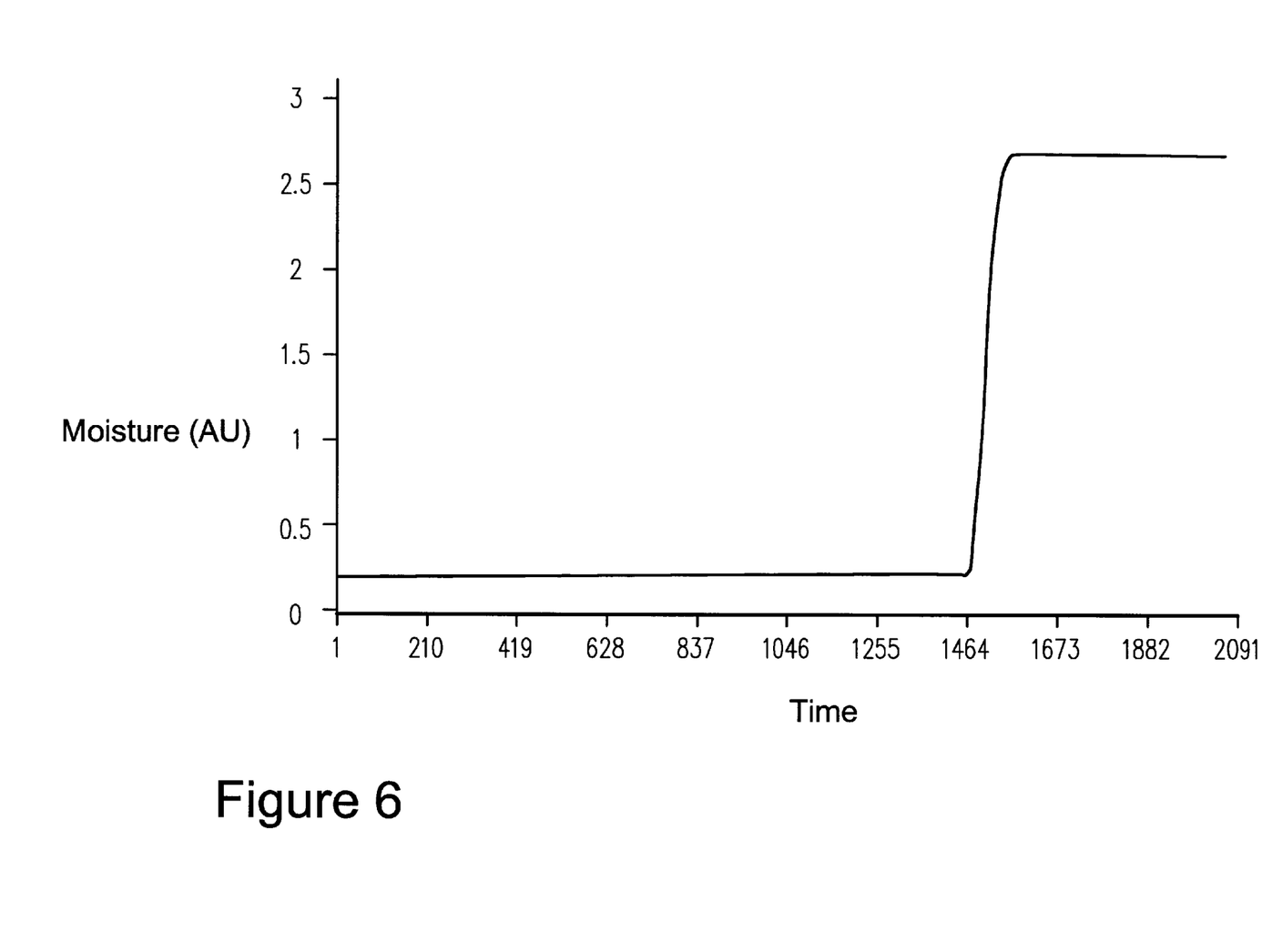
FIG. 6 illustrates the rate of change with time of the moisture level of dental tissue with a smear layer measured using an apparatus according to an embodiment of the invention.

FIGS. 5 and 6 illustrate the rate of change of moisture level obtained using the device according to an embodiment of the invention on two different samples. The results were obtained by drying the surface of the dental tissue under investigation using an air jet, contacting the dried dental tissue with a probe as illustrated in FIG. 1, and applying a sinusoidal drive current to the probe via the circuit illustrated in FIG. 3. The resulting signal is measured, filtered, converted to a DC signal, digitised and processed. The processor calculates rate of change of moisture level with time and outputs the results graphically. These graphical results for a sample containing a smear layer and one without such a layer are shown in FIGS. 5 and 6.

When a tooth is drilled prior to filling, a smear layer may form on the drilled surface. There has been much controversy as to whether such a layer affects the sensitivity of the filled tooth or not. Irrespective of this the moisture content of the smear layer does effect bonding. FIGS. 5 and 6 show that the moisture level in tooth tissues without a smear layer increases earlier than for tooth tissues with a smear layer. Furthermore, the moisture level in dental tissue without a smear layer increases to a value of 10 times that of the value obtained where a smear layer is present. Thus, the presence of a smear level may have a large effect on the bonding.

It will be apparent, that the present embodiment has been described by way of example only and that modifications may be made without the scope of the appended claims.

What is claimed is:

1. An apparatus for measuring the moisture level within enamel, dentine or tooth tissues of a test sample, comprising:
    a probe having two electrodes arranged such that they both contact the enamel, dentine or tooth tissues of the test sample;
    an electrical power source connected between the two electrodes;
    a sensor for sensing the voltage or current produced by said power source across or through the test sample; and
    a signal processor responsive to said measured voltage and/or current to calculate a value indicative of said moisture level within said enamel, dentine or tooth tissues, wherein the two electrodes are arranged coaxially with in insulator layer separating them and a diameter of a tip of said probe is less than 5 mm.

2. An apparatus according to claim 1, wherein said electrodes have a contact surface which is flat.

3. An apparatus according to claim 1, wherein said electrodes have a contact surface which is convex at the tip of said probe.

4. An apparatus according to claim 1, wherein the tip of said probe is conical.

5. An apparatus according to claim 1, wherein the diameter of said probe tip is substantially 1 mm.

6. An apparatus according to claim 1, wherein said power source is an AC source.

7. An apparatus according to claim 6, wherein said AC source is a sinusoidal current source.

8. An apparatus according to claim 6, wherein the apparatus is bandwidth limited and the signals are filtered to reject extraneous interference.

9. An apparatus according to claim 6, further comprising a full wave rectifier, low pass filter and an analogue to digital converter to convert the analogue signal to a digital signal.

10. An apparatus according to claim 9, wherein the analogue to digital converter is a 16 bit or greater analogue to digital converter.

11. An apparatus according to claim 9, wherein the analogue to digital converter has a sampling rate of at least 100 Hz.

12. An apparatus according to claim 1, wherein the impedance of the apparatus is greater than 1 GOhm.

13. An apparatus according to claim 1, further comprising data storage means for storing calibration data.

14. An apparatus according to claim 13, wherein said data storage means comprises calibration data, including at least two sets of values of resistance or conductance with associated moisture level.

15. An apparatus according to claim 14, wherein said data storage means comprises calibration data, including at least two sets of values of resistance or conductance with associated tooth sensitivity.

16. An apparatus according to claim 1, wherein said signal processor is adapted to calculate tooth sensitivity from the variation in the measured values over time.

17. An apparatus according to claim 1, further comprising display means for displaying the calculated moisture level or tooth sensitivity.

18. An apparatus according to claim 17, wherein said display means is a graphical display means adapted to display the variation in moisture level with time.

19. An apparatus according to claim 1, further comprising an alarm set to be activated when the measured values exceed or fall below at least one preset value.

20. A method of measuring the moisture level of enamel, dentine or tooth tissues comprising the steps of:

removing excess surface saliva from an area to be tested of the enamel, dentine or tooth tissues;

contacting said test area with a probe having two electrodes;

connecting an electrical power source between the electrodes;

measuring the current or voltage produced by said electrical power source through or across said test area;

calculating a value indicative of the moisture level of said test area from said measured values, wherein the two electrodes are arranged coaxially with an insulator layer separating them and the diameter of the tip of said probe is less than 5 mm.

21. A method according to claim 20, wherein said electrical power source is an AC power source and the method further comprises the step of converting the AC signal emanating from said test area to a DC signal.

22. A method according to claim 21, further comprising the step of:

converting the analogue signals to digital signals prior to measuring them.

23. A method according to claim 20 further comprising the step of:

comparing the measured values with calibration values.

24. A method according to claim 20 wherein the steps are repeatedly performed over a period of time.

25. A method according to claim 24, further comprising the steps of:

measuring the rate of change of moisture level of the test area over time;

determining the sensitivity of the test area from said rate of change or moisture level.

* * * * *